US007173037B2

(12) United States Patent
Alonso-Alija et al.

(10) Patent No.: US 7,173,037 B2
(45) Date of Patent: Feb. 6, 2007

(54) CARBAMATE-SUBSTITUTED PYRAZOLOPYRIDINES

(75) Inventors: Cristina Alonso-Alija, Haan (DE); Erwin Bischoff, Wuppertal (DE); Klaus Münter, Wülfrath (DE); Johannes-Peter Stasch, Solingen (DE); Elke Stahl, Gladbach (DE); Stefan Weigand, Wuppertal (DE); Achim Feurer, Wilhelmsfeld (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/513,869

(22) PCT Filed: Apr. 25, 2003

(86) PCT No.: PCT/EP03/04304

§ 371 (c)(1),
(2), (4) Date: Jul. 15, 2005

(87) PCT Pub. No.: WO03/095451

PCT Pub. Date: Nov. 20, 2003

(65) Prior Publication Data

US 2006/0052397 A1 Mar. 9, 2006

(30) Foreign Application Priority Data

May 8, 2002 (DE) ............... 102 20 570

(51) Int. Cl.
C07D 471/04 (2006.01)
A61K 31/506 (2006.01)
C07D 231/38 (2006.01)

(52) U.S. Cl. ...................... 514/256; 544/328
(58) Field of Classification Search ............... 544/328; 514/256
See application file for complete search history.

(56) References Cited

FOREIGN PATENT DOCUMENTS

| DE | 19834044 | 2/2000 |
|---|---|---|
| DE | 19834045 | 2/2000 |
| DE | 19846514 | 4/2000 |
| EP | 0 463 756 | 4/1995 |
| WO | 94/28902 | 12/1994 |
| WO | 95/19978 | 7/1995 |
| WO | 98/16223 | 4/1998 |
| WO | 98/16507 | 4/1998 |
| WO | 98/23619 | 6/1998 |
| WO | 99/24433 | 5/1999 |
| WO | 00/06567 | 2/2000 |
| WO | 00/06568 | 2/2000 |
| WO | 00/06569 | 2/2000 |
| WO | 0006567 | 2/2000 |
| WO | 00/21954 | 4/2000 |
| WO | 02/42299 | 5/2002 |
| WO | 02/42300 | 5/2002 |
| WO | 02/42302 | 5/2002 |
| WO | 05/42301 | 5/2002 |
| WO | 0242299 | 5/2002 |
| WO | 0242300 | 5/2002 |
| WO | 0242301 | 5/2002 |
| WO | 0242302 | 5/2002 |
| WO | 02092596 | 11/2002 |
| WO | 03004503 | 1/2003 |

OTHER PUBLICATIONS

Cavalieri, et al., "A Synthesis of Adenine. The Incorporation of Isotopes of Nitrogen and Carbon," *J. Am. Chem. Soc.*, 71, 533-536 (1949).
Li, et al., "Synthesis and Structure—Activity Relationships of 2-Pyridones: A Novel Series of Potent DNA Gyrase Inhibitors as Antibacterial Agents," *J. Med. Chem.*, 39, 3070-3088 (1996).
Beavo, et al., "Primary Sequence of Cyclic Nucleotide Phosphodiesterase Isozymes and the Design of Selective Inhibitors," 11, 150-155 (1990).
Proposed INN: List 88, *WHO Drug Information*, vol. 17 No. 1 (2003).
Ko et al., YC-1, a Novel Activator of Platelet Guanylate Cyclase; Blood, 84, pp. 4226-4233 (1994).
Mülsch et al., Effect of YC-1, an NO-independent, Superoxide-Sensitive Stimulator of Soluble Guanylyl Cyclase, on Smooth Muscle Responsiveness to Nitrovasodilators; Brit. J. Pharm., 120, pp. 681-689 (1997).
Goldberg et al., Stimulation of Human Platelet Guanylate Cyclase by Fatty Acids; J. Biol. Chem., 252, pp. 1279-1285 (1977).
Pettibone et al., A Structurally Novel Stimulator of Guanylate Cyclase with Long-Lasting Hypotensive Activity in the Dog; Euro. J. of Pharmacology, 116, pp. 307-312 (1985).
Yu et al., Vasorelaxant Effect of Isoliquiritigenin, a Novel Soluble Guanylate Cyclase Activator, in Rat Aorta; Brit. J. of Pharmacology, 114, pp. 1587-1594 (1995).
Cavalieri et al., A Synthesis of Adenine: The Incorporation of Isotopes of Nitrogen and Carbon: J. Am. Chem. Soc., 71, pp. 533-536 (1949).
Borsche et al., Über die Kondensation von Säureestern mit Aliphatischen Nitrilen; Liebigs Ann. Chem., 512, pp. 97-111 (1934).
Li et al., Synthesis and Structure-Activity Relationships of 2-Pyridones: A Novel Series of Potent DNA Gyrase Inhibitors as Antibacterial Agents; J. Med. Chem., 39, pp. 3070-3088 (1996).
Beavo et al., Primary Sequence of Cyclic Nucleotide Phosphodiesterase Isozymes and the Design of Selective Inhibitors; TiPS Reviews, 11, pp. 150-155 (1990).
Bischoff et al., A Conscious-rabbit Model to Study Vardenafil Hydrochloride and Other Agents that Influence Penile Erection; Int. J. of Impotence Res., 13, pp. 230-235 (2001).
Bischoff et al., The Oral Efficacy of Vardenafil Hydrochloride for Inducing Penile Erection in a Conscious Rabbit Model; J. of Urology, 165, pp. 1316-1318 (2001).
Bischoff et al., Rabbits as Models for Impotence Research; Int. J. Impotence Res., 13, pp. 146-148 (2001).

*Primary Examiner*—Deepak Rao

(57) ABSTRACT

The present invention relates to compounds which stimulate soluble guanylate cyclase, to the preparation thereof and to the use thereof as medicaments, in particular as medicaments for the treatment of cardiovascular disorders and/or sexual dysfunction.

13 Claims, No Drawings

CARBAMATE-SUBSTITUTED PYRAZOLOPYRIDINES

The present invention relates to compounds which stimulate soluble guanylate cyclase, to the preparation thereof and to the use thereof as medicaments, in particular as medicaments for the treatment of cardiovascular disorders and/or sexual dysfunction.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. CO is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological process, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke, sexual dysfunction and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Some substances which directly stimulate guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Brit. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et. al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569, WO 00/21954 WO 02/42299, WO 02/42300, WO 02/42301, WO 02/42302, WO 02/092596 and WO 03/004503 describe pyrazolopyridine derivatives as stimulators of soluble guanylate cyclase. Also described inter alia therein are pyrazolopyridines having a pyrimidine residue in position 3. Compounds of this type have very high in vitro activity in relation to stimulating soluble guanylate cyclase. However, it has emerged that these compounds have disadvantages in respect of their in vivo properties such as, for example, their behaviour in the liver, their pharmacokinetic behaviour, their dose-response relation or their metabolic pathway.

It was therefore the object of the present invention to provide further pyrazolopyridine derivatives which act as stimulators of soluble guanylate cyclase but do not have the disadvantages detailed above, of the compounds from the prior art.

This object is achieved by the compounds according to claim 1 of the invention. This new class of pyrazolopyridine derivatives is distinguished by having in position 3 a pyrimidine residue which has a particular subsitution pattern, namely a carbamate residue in position 5 of the pyrimidine ring, and an amino group in position 4 of the pyrimidine ring.

The present invention specifically relates to compounds of the formula (I).

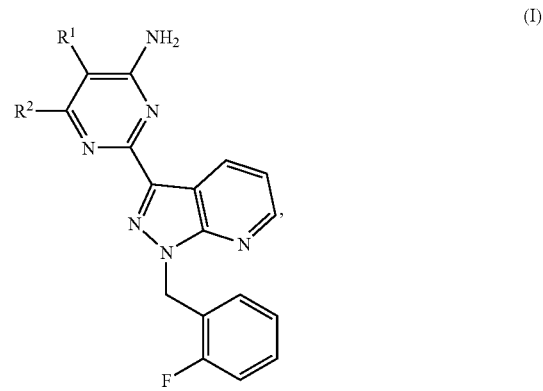

in which
$R^1$ is —$NR^3C(=O)OR^4$,
$R^2$ is hydrogen or $NH_2$,
$R^3$ is hydrogen or $(C_1-C_4)$-alkyl,
$R^4$ is $(C_1-C_6)$-alkyl, and salts, isomers and hydrates thereof.

Preference is given to compounds of the formula (I) in which
$R^1$ is —$NR^3C(=O)OR^4$,
$R^2$ is hydrogen or $NH_2$,
$R^3$ is $(C_1-C_4)$-alkyl,
$R^4$ is $(C_1-C_4)$-alkyl, and salts, isomers and hydrates thereof.

Particular preference is given to compounds of the formula (I) in which
$R^1$ is —$NR^3C(=O)OR^4$,
$R^2$ is $NH_2$,
$R^3$ is methyl or ethyl,
$R^4$ is methyl, ethyl or isopropyl, and salts, isomers and hydrates thereof.

Especial preference is given to the compound methyl-4,6-diamino-2-[1-(2-fluorobenzyl)-1H-pyrazolo[3,4-b]pyridin-3-yl]-5-pyrimidinyl(methyl)carbamate from Example 8:

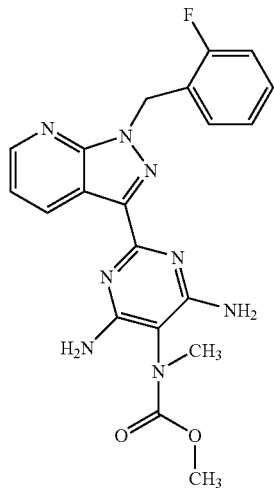

The compounds according to the invention of the formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, p-toluenesulphonic acid, benzenesulphonic acid, naphthaline-disulphonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia or organic amines such as, for example, ethylamine, di- or triethylamine, di- or triethanol amine, dicyclohexylamine, dimethylaminoethanol, arginine, lysine or ethylenediamine.

The compounds according to the invention may exist in tautomeric forms. This is known to the skilled person, and the invention likewise encompasses such forms.

The compounds according to the invention may furthermore be in the form of their possible hydrates.

Alkyl is a linear or branched alkyl radical having, as a rule, 1 to 6, preferably 1 to 4, particularly preferably 1 to 3, carbon atoms, by way of example and preferably methyl, ethyl, n-propyl, isopropyl, tert-butyl, n-pentyl and n-hexyl.

Halogen is for the purposes of the invention fluorine, chlorine, bromine and iodine The present invention also relates to a process for preparing the compounds according to the invention of the formula (I). These can be prepared
[A] by reacting compounds of the formula (Ia)

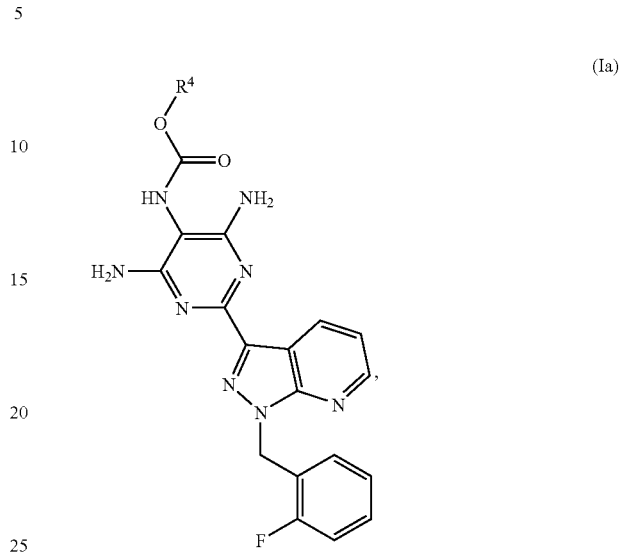

in which
$R^4$ is as defined above,
with compounds of the formula (II)

$$R^3-X^1 \quad (II),$$

in which
$R^3$ is as defined above, and
$X^1$ is a leaving group such as, for example, halogen, preferably iodine, or mesylate,
where appropriate in an organic solvent with cooling to give compounds of the formula (I), or
[B] by reacting the compound of the formula (III)

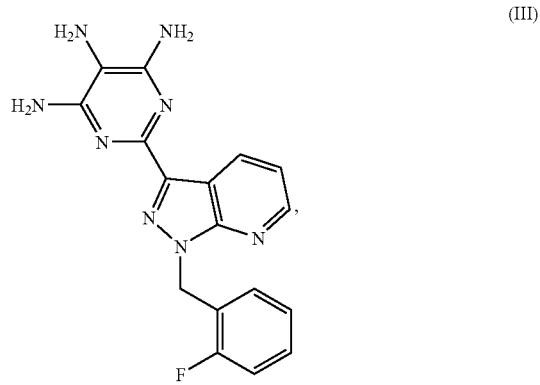

with compounds of the formula (IV)

in which

R⁴ is as defined above, where appropriate in an organic solvent to give compounds of the formula (Ia), or

[C] by reacting the compound of the formula (V)

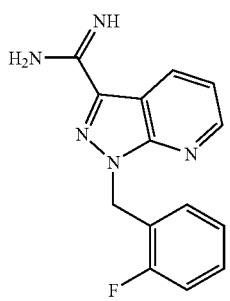

(V)

with compounds of the formula (VI)

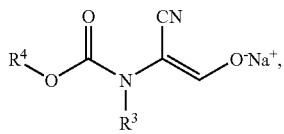

(VI)

in which

R³ and R⁴ are as defined above, where appropriate in an organic solvent with heating to give compounds of the formula (Ib)

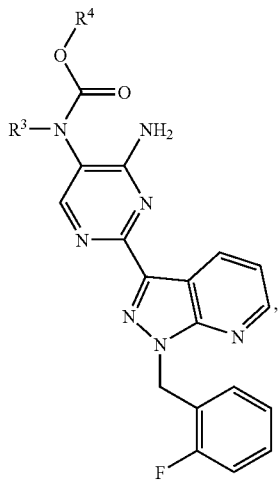

(Ib)

in which

R³ and R⁴ are as defined above.

The compounds of the formulae (II) and (IV) are commercially available or known from the literature or can be prepared in a manner known to the skilled person.

The compound of the formula (III) can be prepared as shown in the following reaction scheme:

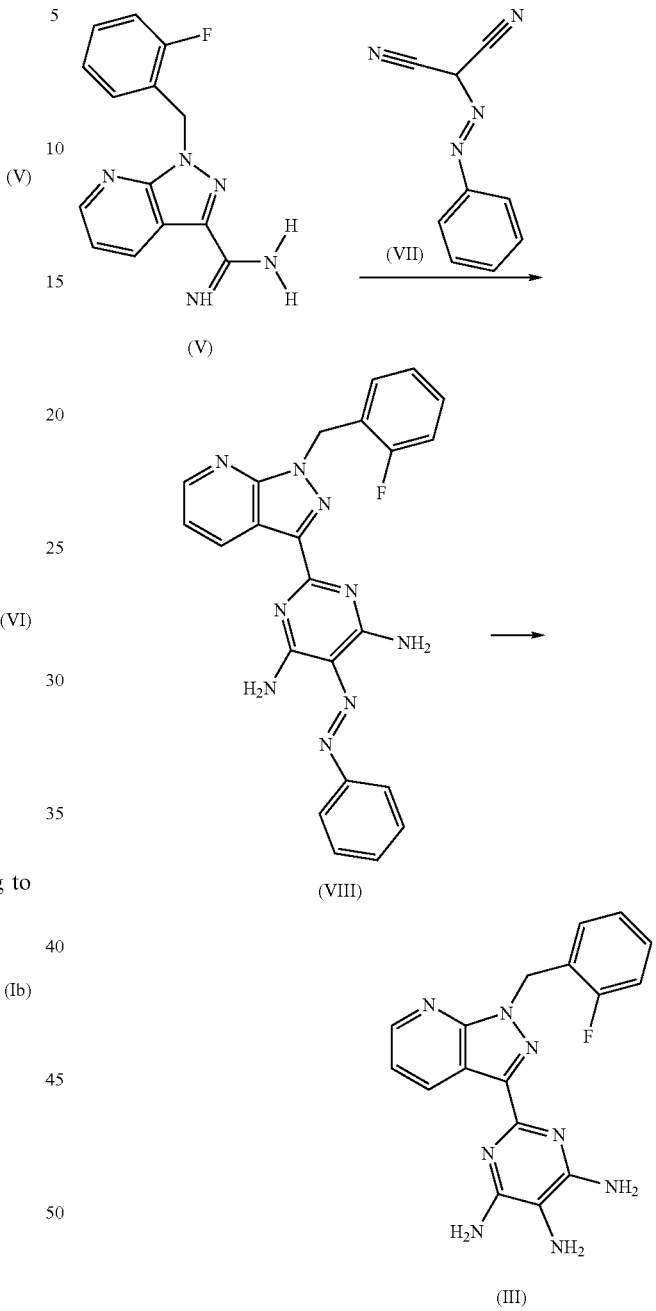

Compound (III) is obtainable in a two-stage synthesis by reacting compound (V) with compound (VII) to give compound (VIII) in accordance with process step [C] and subsequently hydrogenating compound (VIII) with aqueous Raney nickel. The hydrogenation can be carried out in an organic solvent, for example dimethylformamide, preferably under elevated pressure, for example under 50 to 70 bar, preferably under 65 bar, stirring the reaction solution for several hours, for example for 22 hours, at elevated temperature, for example at 40 to 80° C., preferably at 60° C. to 65° C.

The compound (VII) can be prepared in analogy to L. F. Cavalieri, J. F. Tanker, A. Bendich, J. Am. Chem. Soc., 1949, 71, 533.

The compound (V) can be prepared as shown in the following reaction scheme:

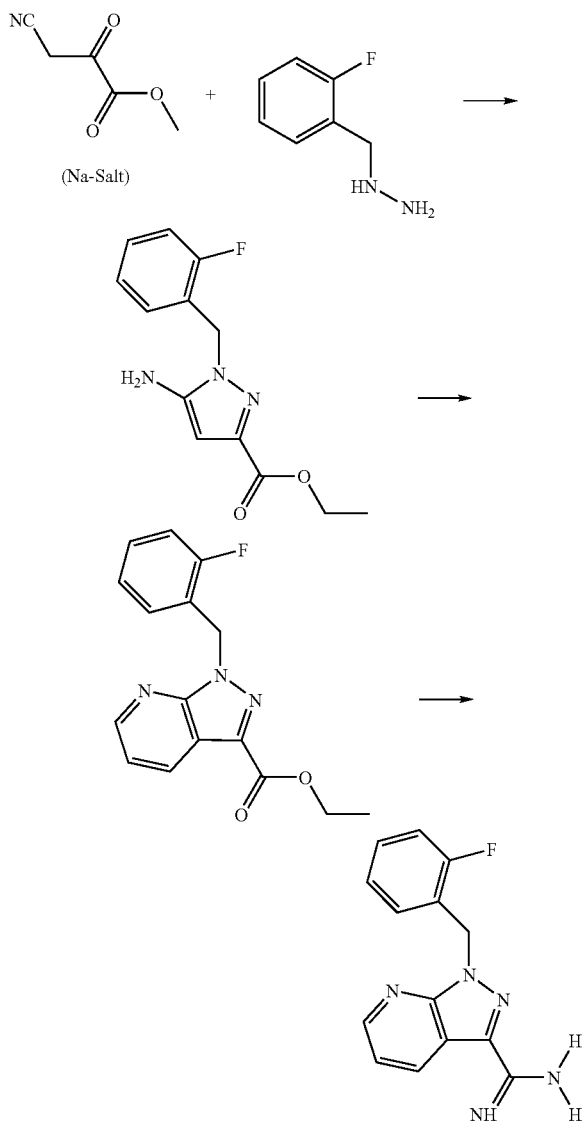

compound (V) is obtainable in a multistage synthesis from the sodium salt of ethyl cyanopyruvate, which is known from the literature (Borsche and Manteuffel, Liebigs. Ann. Chem. 1934, 512, 97). Reaction thereof with 2-fluorobenzylhydrazine while heating under a protective gas atmosphere in an inert solvent such as dioxane results in ethyl 5-amino-1-(2-fluorobenzyl)pyrazole-3-carboxylate, which can be cyclized by reaction with dimethylaminoacrolein in acidic medium under a protective gas atmosphere and heating to give the corresponding pyridine derivative. This pyridine derivative, ethyl 1-(2-fluorobenzyl)-1H-pyrazolo[3,4-b]pyridin-3-carboxylate, is converted by a multistage sequence consisting of conversion of the ester with ammonia into the corresponding amine, dehydration with a dehydrating agent such as trifluoroacetic anhydride to give the corresponding nitrile derivative, reacting the nitrile derivative with sodium ethoxide and finally reaction with ammonium chloride into the compound (V).

The compounds of the formula (VI) can be synthesized by methods known to the skilled person from the corresponding carbamates by reaction with ethyl formate. The carbamates can be prepared in analogy to Q. Li, D. T. Chu, A. Claiborne, C. S. Cooper, C. M. Lee, J. Med. Chem. 39 (1996) 3070–3088.

Reaction of the compounds of the formulae (Ia) and (II) to give compounds of the formula (I) can be carried out by using the reactants in equimolar amounts in an organic solvent, for example dimethylformamide or tetrahydrofuran, preferably in the presence of 1 to 2 equivalents, preferably 1.1 to 1.5 equivalents, of a base such as, for example, sodium hydride or sodium N,N-bistrimethylsilylamide, preferably under atmospheric pressure and with stirring of the reaction solution for a few hours, for example for 1 hour, with cooling, for example at −10° C. to room temperature, preferably at 0° C.

Reaction of the compounds of the formulae (III) and (IV) to give the compounds of the formula (Ia) can be carried out by using the reactants in equimolar amounts in an organic solvent, for example an organic base, preferably pyridine, preferably under atmospheric pressure and with stirring of the reaction solution for several hours, for example for 12 hours, at 0° C. to room temperature, preferably at room temperature.

Reaction of compounds of the formulae (V) and (VI) to give compounds of the formula (Ib) or of compounds of the formulae (V) and (VII) to give compounds of the formula (VIII) can be carried out by using the reactants in equimolar amounts or with use of the compound of the formula (VI) in slight excess in an organic solvent such as, for example, in a hydrocarbon such as toluene or xylene or in N,N-dimethylformamide, preferably in the presence of 2–3 equivalents, preferably 2 equivalents, of a base such as, for example, triethylamine or sodium methanolate, preferably under atmospheric pressure and with stirring of the reaction solution for several hours, for example for 9 hours, at elevated temperature, for example at 80–160° C., preferably at 100–150° C., in particular at 110° C.

The compounds according to the invention of the formula (I) show a valuable range of pharmacological effects which could not have been predicted.

The compounds according to the invention of the formula (I) bring about vasorelaxation and an inhibition of platelet aggregation and lead to a reduction in blood pressure and an increase in coronary blood flow. These effects are mediated by direct stimulation of soluble guanylate cyclase and an intracellular increase in cGMP. In addition, the compounds according to the invention of the formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischaemias such as myocardial infarction, stroke, transient ischaemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, glaucoma, pulmonary hypertension, gastroparesis and incontinence.

The compounds according to the invention of the formula (I) are also suitable for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occuring after strokes (post stroke dementia), post-traumatic brain syndrome, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jakob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention of the formula (I) are furthermore also suitable for controlling cerebral blood flow and thus represent effective agents for controlling migraine.

The compounds according to the invention of the formula (I) are also suitable for the prophylaxis and control of the sequelae of cerebral infarctions such as stroke, cerebral ischaemias and craniocerebral trauma. They can likewise be employed for controlling states of pain.

In addition, the compounds according to the invention of the formula (I) have an anti-inflammatory effect and can therefore be employed as anti-inflammatory agents.

Furthermore the present invention also encompasses the combination of at least one compound according to the invention of the formula (I) with one or more organic nitrates or NO donors.

Organic nitrates and NO donors for the purposes of the invention are generally substances which display their therapeutic effect via release of NO or NO species. Mention may be made by way of example and preferably of: sodium nitroprusside, nitroglycerine, isosorbide dinitrate, isosorbide mononitrate, molsidomine and SIN-1.

In addition, the present invention also encompasses the combination with one or more compounds which inhibit breakdown of cyclic guanosine monophosphate (cGMP). These are preferably inhibitors of phosphodiesterases 1, 2 and 5; nomenclature of Beavo and Reifsnyder (1990), TiPS 11 pp. 150 to 155. Particularly preferred in this connection are inhibitors of phosphodiesterase 5 (PDE V inhibitors), especially one of the compounds sildenafil (Viagra™, EP-A 0 463 756, WO 94/28902), vardenafil (WO 99/24433) or tadalafil (WO 95/19978). These inhibitors potentiate the effect of the compounds according to the invention, and the desired pharmacological effect is increased.

Biological Investigations

Vasorelaxant Effect in Vitro

Rabbits are stunned by a blow to the back of the neck and are exsanguinated. The aorta is removed, freed of adherent tissue and divided into rings 1.5 mm wide, which are put singly under tension in 5 ml organ baths containing carbogen-gassed Krebs-Henseleit solution at 37° C. with the following composition (mM): NaCl:119; KCl:4.8; $CaCl_2 \times 2H_2O$:1; $MgSO_4 \times 7H_2O$:1.4; $KH_2PO_4$:1.2; $NaHCO_3$:25; Glucose:10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increasing dosage in each case, and the height of the contraction is compared with the height of the contraction reached in the last preceding run. The concentration necessary to reduce the height of the control value by 50% ($IC_{50}$) is calculated from this. The standard application volume is 5 μl, and the DMSO content in the bath solution corresponds to 0.1%.

The $IC_{50}$ for the compound of Example 1 is 670 nM, and the corresponding value for the compound of Example 8 is 500 nM.

Rabbit Model

Adult male chinchilla rabbits weighing 3–5 kg are adapted to being kept singly for several days after delivery. They have free access to water and can take feed for two hours a day. The animals are kept in a 10/14-hour day/night rhythm (light on from 8.00 h), and the room temperature is 22–24° C.

Three to six animals are used in each treatment group and are weighed immediately before the start of the test. For the i.v. administration, the substances are dissolved in Transcutol (GATTEFOSSE GmbH) and diluted in the ratio 3/7 with a 20% strength Cremophor solution (Cremophor (BASF), water). A volume of 0.5 ml/kg is injected into the ear vein. Water-soluble substances are injected in 0.9% sodium chloride solution.

For oral administration, the test substances are dissolved in a 6:10:9.69 glycerol:water:polyethylene glycol mixture and administered by gavage in a volume of 1 ml/kg.

Under resting conditions, the rabbit penis is invisible in the pubic region and is completely covered by the penis skin. The erection is assessed by measuring the length of the protruding penis with a slide calliper. The measurement is carried out 5, 10, 15, 30, 45, 60 and 120 minutes after administration of the substance and, after oral administration, additionally after 3, 4, 5 and 6 hours. The animals are for this purpose removed from the cage each time, held firmly by the neck fur and the rear paws, turned on their backs and measured. Corresponding solvent controls are carried out. (Compare reference: E. Bischoff, K. Schneider, Int. J. of Impotence Res. 2001, 13, 230–235; E. Bischoff, U. Niewoehner, H. Haning, M. Es Sayed, T. Schenke, K. H. Schlemmer, The Journal of Urology, 2001, 165, 1316–1318; E. Bischoff, Int. J. Impotence Res. 2001, 13, 146–148).

The minimal effective dose of the compound of Example 8 on oral administration is 0.03 mg/kg (with simultaneous administration of 0.2 mg/kg i.v. sodium nitroprusside SNP).

Determination of Pharmacokinetic Parameters after Intravenous and Oral Administration The substance to be investigated is administered intravenously as solution to animals (e.g. mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS/MS. The plasma concentration/time courses found in this way are used to calculate the pharmacokinetic parameters by means of a validated pharmacokinetic computer programme.

After oral administration of 0.3 and 1.0 mg/kg (as solution in Solutol:EtOH:Wasser 1:1:8) to rats, the compound of Example 8 shows the following plasma concentrations (AUC):

AUCstand (0.3 mg/kg)=0.326 [kg*h/L]
AUCstand (1.0 mg/kg)=0.548 [kg*h/L]

Inhibition of Cytochrome P450 Enzymes

The potential for inhibition of P-450 isoenzymes which are important for metabolism is investigated automatically in a 96-well format. Two different assays are used for this.

In the assay based on the formation of fluorescent metabolites, recombinant enzymes (e.g. CYP1A2, 2C8, 2C9, 2C19, 2D6 or 3A4) and in general substrates containing fluorescein or coumarin partial structures are employed. In each case one substrate concentration and 8 concentrations of the potential inhibitor are used. After incubation with the particular recombinant CYP enzyme, a fluorescence reader is used to measure the extent of fluorescent metabolites compared with the control (without inhibitor), and an $IC_{50}$ is calculated [Anal. Biochem. 248, 188 (1997)].

In the 2nd assay, human liver microsomes are used as enzyme source, and the CYP isoform-selective substrates used are phenacetin (CYP1A2), diclofenac (CYP2C9), dextromethorphan (CYP2D6) and midazolam (CYP3A4). The formation of the particular metabolite is measured using LC-MS/MS. Assuming that inhibition is competitive, $K_i$ values are calculated from the reduction in metabolite formation compared with the control (1 substrate and 3 inhibitor concentrations).

Induction of Cytochrome P450 Enzymes in Human Liver Cell Cultures

To investigate the potential for side effects of the substances according to the invention in relation to induction of cytochrome P450 enzymes, primary human hepatocytes are cultured with a cell density of $2.5 \times 10^5$ cells between two layers of collagen in 24-well microtitre plates at 37° C. with 5% $CO_2$ for 8 days. The cell culture medium is changed each day.

After 48 hours in culture, the hepatocytes are treated with different concentrations of the test substances, comparing with the inducers rifampicin (RIF; 50 µM), omeprazole (OME; 100 µM) and phenobarbital (PB; 2 mM), in duplicate determination for 5 days. The final concentrations of the test substances are 0.01–10 µg/ml.

The inductive effect of the test substances on the cytochrome (CYP) P450 enzymes 1A2, 2B6, 2C19 and 3A4 is determined by adding the substrates 7-ethoxyresorufin (CYP1A2), [$^{14}$C]-S-mephenytoin (CYP2B6 and 2C19) and [$^{14}$C]-testosterone (CYP3A4) to the cell cultures on day 8. The inductive potential of the test substances is found from the activities, measured in this way, of CYP1A2, 2B6, 2C19 and 3A4 enzymes of treated cells compared with untreated cells. Table 1 below shows the results of the compound of Example 8 compared with the inducers RIF, PB and OME:

TABLE 1

Inductive effect on liver enzymic activities in human hepatocyte cultures after incubation for 8 days (standardized)

| | Concentration | CYP1A2 | CYP2B6 | CYP2C19 | CYP3A4 |
|---|---|---|---|---|---|
| Control | 0 | 1.0 | 1.0 | 1.0 | 1.0 |
| RIF | 50 µM | n.d. | 5.15 | 15.21 | 9.15 |
| PB | 2000 µM | n.d. | 14.69 | 4.00 | 6.70 |
| OME | 100 µM | 28.57 | 1.54 | 1.61 | 1.45 |
| Example 8 | 0.01 µg/ml | 0.76 | 1.92 | 1.30 | 1.37 |
| | 0.1 µg/ml | 0.70 | 1.62 | 1.30 | 1.60 |
| | 1.0 µg/ml | 0.90 | 1.85 | 1.12 | 1.51 |
| | 10 µg/ml | 1.38 | 2.54 | 1.97 | 3.47 | n.d. = not determined

The present invention further relates to medicaments which comprise at least one compound according to the invention, preferably together with one or more pharmacologically acceptable excipients or carriers, and to the use thereof for the aforementioned purposes.

The active ingredient may have systemic and/or local effects. For this purpose, it can be administered in a suitable way such as, for example, oral, parenteral, pulmonary, nasal, sublingual, lingual, buccal, rectal, transdermal, conjunctival, topical or as implant.

The active ingredient can be administered in administration forms suitable for these administration routes.

Suitable for oral administration are known administration forms which deliver the active ingredient rapidly and/or in a modified manner, such as, for example, tablets (uncoated and coated tablets, e.g. tablets provided with enteric coatings or film-coated tablets), capsules, sugar-coated tablets, granules, pellets, powders, emulsions, suspensions, solutions and aerosols.

Parenteral administration can take place with avoidance of an absorption step (intravenous, intraarterial, intracardiac, intraspinal or intralumbar) or with inclusion of an absorption (intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates and sterile powders.

Suitable for the other routes of administration are, for example, pharmaceutical forms for inhalation (inter alia powder inhalers, nebulizers), nasal drops/solutions, sprays; tablets or capsules for lingual, sublingual or buccal administration, suppositories, preparations for the ears and eyes, vaginal capsules, aqueous suspensions (lotions, shaking mixtures), lipophilic suspensions, ointments, creams, milk, pastes, dusting powders or implants, such as, for example, stents.

The active ingredients can be converted in a manner known per se into the stated administration forms. This takes place with use of inert non-toxic, pharmaceutically suitable excipients. These include, inter alia, carriers (for example microcrystalline cellulose), solvents (for example liquid polyethylene glycols), emulsifiers (for example sodium dodecyl sulphate), dispersants (for example polyvinylpyrrolidone), synthetic and natural biopolymers (for example albumin), stabilizers (for example antioxidants such as ascorbic acid), colourings (for example inorganic pigments such as iron oxides) or masking flavours and/or odours. The active ingredient can, where appropriate, be present also in microencapsulated form in one or more of the carriers indicated above.

The therapeutically effective compound of the formula (I) should be present in the pharmaceutical preparations detailed above in a concentration of about 0.1 to 99.5, preferably of about 0.5 to 95, % by weight of the complete mixture.

The pharmaceutical preparations detailed above may, apart from the compound according to the invention of the formula (I) also contain other active pharmaceutical ingredients.

It has generally proved to be advantageous both in human and in veterinary medicine to administer the active ingredient according to the invention in total amounts of about 0.001 to about 50, preferably 0.001 to 10, mg/kg of body weight every 24 hours, where appropriate in the form of a plurality of single doses, to achieve the desired results. A single dose contains the active ingredient according to the invention preferably in amounts of about 0.001 to about 30, in particular 0.001 to 3, mg/kg of body weight.

The present invention is explained in more detail below by means of non-restrictive preferred examples. Unless indicated elsewhere, all quantitative data relate to percentages by weight. Solvent ratios, dilution ratios and concentration data for liquid/liquid solutions relate in each case to volume.

| Abbreviations: | |
| --- | --- |
| ACN | acetonitrile |
| BABA | n-butyl acetate/n-butanol/glacial acetic acid/phosphate buffer pH 6 (50:9:25.15; org. phase) |
| conc. | concentrated |
| DCI | direct chemical ionization (in MS) |
| DCM | dichloromethane |
| DIEA | N,N-diisopropylethylamine |
| DMSO | dimethyl sulphoxide |
| DMF | N,N-dimethylformamide |
| EA | ethyl acetate |
| EI | electron impact ionization (in MS) |
| ESI | electrospray ionization (in MS) |
| h | hour |
| HPLC | high pressure, high performance liquid chromatography |
| LC-MS | coupled liquid chromatography/mass spectroscopy |
| LDA | lithium diisopropylamide |
| MCPBA | m-chloroperoxybenzoic acid |
| m.p. | melting point |
| MS | mass spectroscopy |
| NMR | nuclear magnetic resonance spectroscopy |
| $R_f$ | retention index (in TLC) |
| RP-HPLC | reverse phase HPLC |
| RT | room temperature |
| $R_t$ | retention time (in HPLC) |
| sat. | saturated |
| THF | tetrahydrofuran |
| TLC | thin layer chromatography |

Mobile Phases for Thin-layer Chromatography:
T1 E1: toluene/ethyl acetate (1:1)
T1 EtOH1: toluene/ethanol (1:1)
C1 E1: cyclohexane/ethyl acetate (1:1)
C1 E2: cyclohexane/ethyl acetate (1:2)

LCMS and HPLC Methods:

Method 1 (LCMS)

Instrument: Micromass Platform LCZ, HP1100; column: Symmetry C18, 50 mm×2.1 mm, 3.5 µm; eluent A: acetonitrile+0.1% formic acid, eluent B: water+0.1% formic acid; gradient: 0.0 min 10% A→4.0 min 90% A→6.0 min 90% A; oven: 40° C.; flow rate: 0.5 ml/min; UV detection: 208–400 nm.

Method 2 (LCMS)

Instrument: Micromass Quattro LCZ, HP1100; column: Symmetry C18, 50 mm×2.1 mm, 3.5 µm; eluent A: acetonitrile+0.1% formic acid, eluent B: water+0.1% formic acid; gradient: 0.0 min 10% A→4.0 min 90% A→6.0 min 90% A; oven: 40° C.; flow rate: 0.5 ml/min; UV detection: 208–400 nm.

Method 3 (LCMS)

Instrument: Waters Alliance 2790 LC; column: Symmetry C18, 50 mm×2.1 mm, 3.5 µm; eluent A: water+0.1% formic acid, eluent B: acetonitrile+0.1% formic acid; gradient: 0.0 min 5% B→5.0 min 10% B→6.0 min 10% B; temperature: 50° C.; flow rate: 1.0 ml/min; UV detection: 210 nm.

Method 4 (HPLC)

Instrument: HP 1100 with DAD; column: Kromasil RP-18, 60 mm×2 mm, 3.5 µm; eluent: A=5 ml of $HClO_4$/l of $H_2O$, B=ACN; gradient: 0 min 2% B, 0.5 min 2% B, 4.5 min 90% B, 6.5 min 90% B; flow rate: 0.75 ml/min; temp.: 30° C.; detection UV 210 nm.

Preparative RP-HPLC

Column: YMC gel; eluent: acetonitrile/water (gradient); flow rate: 50 ml/min; temp.: 25° C.; detection UV 210 nm.

Starting Compounds:

EXAMPLE 1A

Ethyl 5-amino-1-(2-fluorobenzyl)pyrazole-3-carboxylate

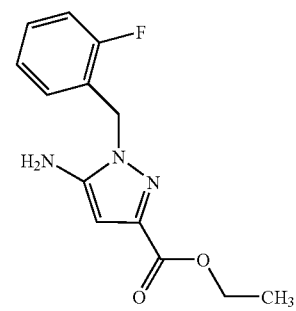

111.75 g (75 ml, 0.98 mol) of trifluoroacetic acid are added to 100 g (0.613 mol) of sodium salt of ethyl cyanopyruvate (prepared in analogy to Borsche and Manteuffel, Liebigs Ann. 1934, 512, 97) in 2.5 l of dioxane under argon with efficient stirring at room temperature, and the mixture is stirred for 10 minutes during which much of the precursor dissolves. Then 85.93 g (0.613 mol) of 2-fluorobenzylhydrazine are added, and the mixture is heated under reflux overnight. After cooling, the crystals of sodium trifluoroacetate which have separated out are filtered off with suction and washed with dioxane, and the solution is reacted further as it is.

EXAMPLE 2A

Ethyl 1-(2-fluorobenzyl)-1H-pyrazolo[3,4-b]pyridine-3-carboxylate

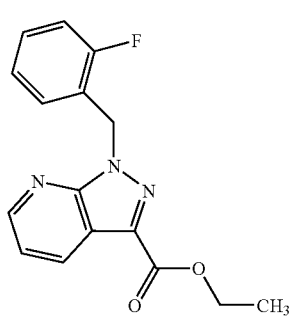

The solution obtained from Example 1A is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is added to 2 l of water and extracted three times with 1 l of ethyl acetate each time. The combined organic phases are dried with magnesium sulphate and concentrated in a rotary evaporator. Chromatography is carried out on 2.5 kg of silica gel, eluting with a toluene/toluene-ethyl acetate=4:1 gradient. Yield: 91.6 g (49.9% of theory over two stages).

Melting point 85° C.

$R_f$ (SiO$_2$, T1 E1): 0.83

EXAMPLE 3A 1-(2-Fluorobenzyl)-1H-pyrazolo[3,4-b]pyridine-3-carboxamide

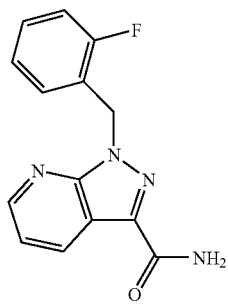

10.18 g (34 mmol) of the ester obtained in Example 2A are introduced into 150 ml of methanol which has been saturated with ammonia at 0–10° C. The mixture is stirred at room temperature for two days and then concentrated in vacuo.

$R_f$ (SiO$_2$, T1 E1): 0.33

EXAMPLE 4A

3-Cyano-1-(2-fluorobenzyl)-1H-pyrazolo[3,4-b]pyridine

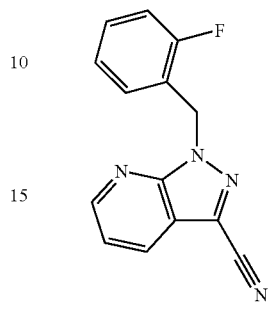

36.1 g (133 mmol) of 1-(2-fluorobenzyl)-1H-pyrazolo[3,4-b]pyridine-3-carboxamide from Example 3A are dissolved in 330 ml of THF, and 27 g (341 mmol) of pyridine are added. Then, over the course of 10 minutes, 47.76 ml (71.66 g, 341 mmol) of trifluoroacetic anhydride are added, during which the temperature rises to 40° C. The mixture is stirred at room temperature overnight. It is then added to 1 l of water and extracted three times with 0.5 l of ethyl acetate each time. The organic phase is washed with saturated sodium bicarbonate solution and with 1N hydrochloric acid, dried with magnesium sulphate and concentrated in a rotary evaporator.

Yield: 33.7 g (100% of theory)

Melting point: 81° C.

$R_f$ (SiO$_2$, T1 E1): 0.74

EXAMPLE 5A

Methyl 1-(2-fluorobenzyl)-1H-pyrazolo[3,4-b]pyridine-3-carboximidate

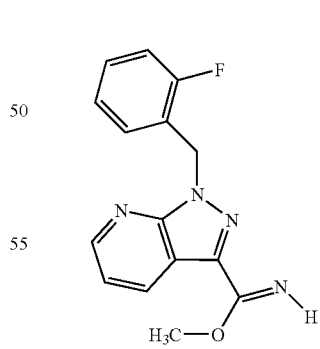

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine (from Example 4A) are added. The mixture is stirred at room temperature for 2 hours and the resulting solution is employed directly for the next stage.

EXAMPLE 6A 1-(2-Fluorobenzyl)-1H-pyrazolo[3,4-b]pyridine-3-carboxamidine

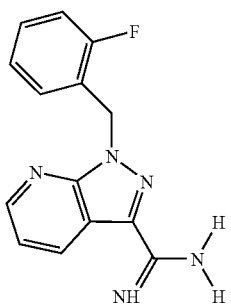

The solution of methyl 1-(2-fluorobenzyl)-1H-pyrazolo[3,4-b]pyridine-3-carboximidate in methanol obtained from Example 5A is mixed with 33.76 g (32.19 ml, 562 mmol) of glacial acetic acid and 9.28 g (173 mmol) of ammonium chloride and stirred under reflux overnight. The solvent is evaporated in vacuo, the residue is thoroughly triturated with acetone, and the precipitated solid is filtered off with suction. It is added to 2 l of water, 31.8 g of sodium carbonate are added while stirring, the mixture is extracted three times with a total of 1 l of ethyl acetate, and the organic phase is dried with magnesium sulphate and evaporated in vacuo.

Yield 27.5 g (76.4% of theory over two stages)
m.p.: 86° C.
$R_f$ (SiO$_2$, T1 EtOH1): 0.08

EXAMPLE 7A

2-[1-(2-Fluorobenzyl)-1H-pyrazolo[3,4-b]pyridin-3-yl]-5-[(E)phenyldiazenyl]4,6-pyrimidinediamine

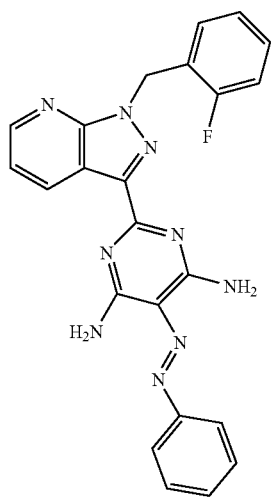

3.87 g of sodium methanolate and then 12.2 g (71.7 mmol) of phenylazomalononitrile (L. F. Cavalieri, J. F. Tanker, A. Bendich, J. Am. Chem. Soc., 1949, 71, 533) are added to a stirred solution of 21.92 g (71.7 mmol) of 1-(2-fluorobenzyl)-1H-pyrazolo[3,4-b]pyridine-3-carboxamidine in N,N-dimethylformamide from Example 6A. The mixture is stirred at 110° C. overnight and allowed to cool. The solid which precipitates is filtered off with suction and washed with ethanol. Drying results in 23 g (73% of theory) of the target compound.

EXAMPLE 8A

2-[1-(2-Fluorobenzyl)-1H-pyrazolo[3,4-b]pyridin-3-yl]-4,5,6-pyrimidinetriamine trihydrochloride

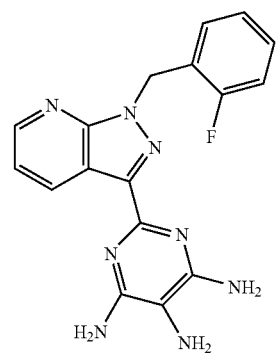

5 g (11.38 mmol) of 2-[1-(2-fluorobenzyl)-1H-pyrazolo[3,4-b]pyridin-3-yl]-5-[(E)-phenyldiazenyl]-4,6-pyrimidinediamine from Example 7A are hydrogenated with 800 mg of 50% Raney nickel in water in 60 ml of DMF under a pressure of 65 bar of hydrogen at 62° C. for 22 hours. The catalyst is filtered off with suction through kieselguhr, and the solution is evaporated in vacuo and stirred with 5N hydrochloric acid. The yellowish brown precipitate which separates out is filtered off with suction and dried. 3.1 g (59.3% of theory) of the targeted compound are obtained. The free base is obtained by shaking with dilute sodium bicarbonate solution and extracted with ethyl acetate. The solid insoluble in both phases is filtered off with suction. The ethyl acetate phase also contains small amounts of the free base.

EXAMPLE 9A

Methyl cyanomethyl(methyl)carbamate

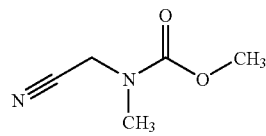

prepared in analogy to: Q. Li, D. T. Chu, A. Claiborne, C. S. Cooper, C. M. Lee, J. Med. Chem. 1996, 39, 3070–3088.

EXAMPLE 10A

Sodium (E)-2-cyano-2-[(methoxycarbonyl)(methyl)amino]ethenolate

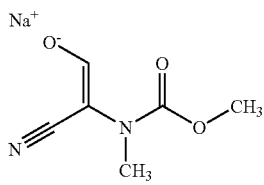

0.46 g (0.01 mmol) of sodium methoxide is added under argon to tetrahydrofuran (solution A). Then 1.00 g (0.01 mmol) of methyl cyanomethyl(methyl)carbamate from Example 9A is added to 1.73 g (0.02 mmol) of ethyl formate. Solution A is slowly added dropwise to this mixture. The mixture is stirred at RT overnight. The solvent is concentrated in vacuo in a rotary evaporator, and diethyl ether is added to the residue. The crystals which have separated out are filtered off with suction and dried under high vacuum.

Yield: 1.05 g (76% of theory).

HPLC (Method 4): $R_t$=1.35 ml.

$^1$H-NMR (200 MHz, DMSO-$d_6$): δ=2.90 (d, 1H), 3.35 (s, 3H), 3.47 (s, 3H).

EXAMPLES

Example 1

Methyl 4-amino-2-[1-(2-fluorobenzyl)-1H-pyrazolo[3,4-b]pyridin-3-yl]-5-pyrimidinyl(methyl)carbamate

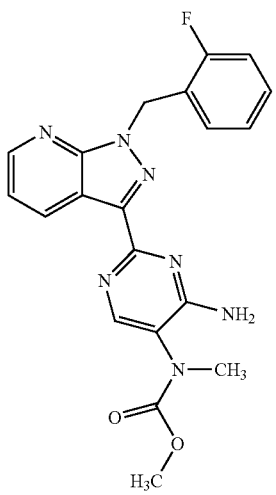

Under argon, 0.80 g (2.61 mmol) of 1-(2-fluorobenzyl)-1H-pyrazolo[3,4-b]pyridine-3-carboxamidine from Example 6A, 0.51 g (2.86 mmol) of sodium (E)-2-cyano-2-[(methoxycarbonyl)(methyl)amino]ethenolate from Example 10A and 0.53 g (0.73 ml, 5.23 mmol) of triethylamine are added to 50 ml of toluene. The mixture is heated under reflux for 9 hours. It is then cooled to RT again and is mixed and extracted with dichloromethane and water. The organic phase is dried over magnesium sulphate, filtered and concentrated in vacuo in a rotary evaporator. The residue is mixed with 5 ml of diethyl ether and crystallizes therewith. The crystals are filtered off with suction, dried and purified by preparative RP-HPLC.

Yield: 20.2 mg (2% of theory)

LC/MS (Method 2): $R_t$=3.01 min

MS (EI): m/z=408 (M+H)$^+$ $^1$H-NMR (300 MHz, DMSO-$d_6$): δ=3.09 (s, 3H), 3.29 (s, 3H), 5.83 (s, 2H), 7.09–7.42 (m, 5H), 8.20 (s, 1H), 8.64 (dd, 1H). 8.94 (dd, 1H), 9.27 (br. s, 2H).

Example 2

Ethyl 4,6-diamino-2-[1-(2-fluorobenzyl)-1H-pyrazolo[3,4-b]pyridin-3-yl]-5-pyrimidinylcarbamate

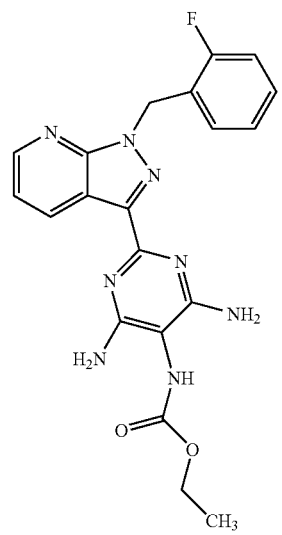

107.35 mg (0.31 mmol) of 2-[1-(2-fluorobenzyl)-1H-pyrazolo[3,4-b]pyridin-3-yl]-4,5,6-pyrimidinetriamine trihydrochloride from Example 8A are added to 5 ml of pyridine, and the mixture is cooled to 0° C. 33.25 mg (0.31 mmol) of ethyl chloroformate are added, and the reaction is left to stir at RT overnight. The pyridine is evaporated in vacuo in a rotary evaporator, and the residue is purified by preparative RP-HPLC.

Yield: 56.2 mg (43% of theory)

LC/MS (Method 1): $R_t$=2.66 min

MS (EI): m/z=423 (M+H)$^+$ $^1$H-NMR (300 MHz, DMSO-$d_6$): δ=1.17–1.33 (m, 3H), 3.97–4.14 (m, 2H), 5.80 (s, 2H), 6.14 (br. s, 4H), 7.07–7.17 (m, 2H), 7.22 (t, 1H). 7.29–7.40 (m, 2H), 1H), 8.60 (d, 1H), 9.07 (d, 1H).

Example 3

Isopropyl 4,6-diamino-2-[1-(2-fluorobenzyl)-1H-pyrazolo[3,4-b]pyridin-3-yl]-5-pyrimidinylcarbamate

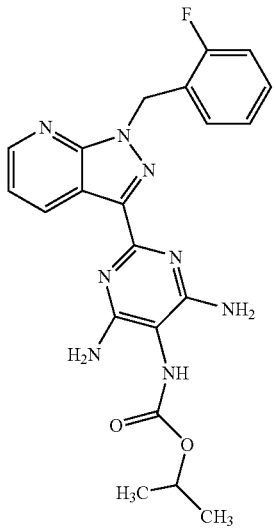

Prepared in analogy to Example 2 with 150 mg (0.43 mmol) of 2-[1-(2-fluorobenzyl)-1H-pyrazolo[3,4-b]pyridin-3-yl]-4,5,6-pyrimidinetriamine trihydrochloride from Example 8A, 7.5 ml of pyridine and 52.47 mg (0.43 mmol) of isopropyl chloroformate. The residue is taken up in a dichloromethane/methanol mixture, filtered and dried.

Yield: 165 mg (88% of theory)

LC/MS (Method 1): $R_t$=2.84 min

MS (EI): m/z=437 (M+H)$^+$ $^1$H-NMR (300 MHz, DMSO-d$_6$): δ=1.26 (d, 6H), 4.82 (quin., 1H), 5.92 (s, 2H), 7.07–7.20 (m, 2H), 7.25 (t, 1H). 7.31–7.43 (m, 2H), 7.47–7.57 (m, 1H), 8.16 (br. s, 1H), 8.74 (dd, 1H), 8.98 (dd, 1H).

Example 4

Neopentyl 4,6-diamino-2-[1-(2-fluorobenzyl)-1H-pyrazolo[3,4-b]pyridin-3-yl]-5-pyrimidinylcarbamate

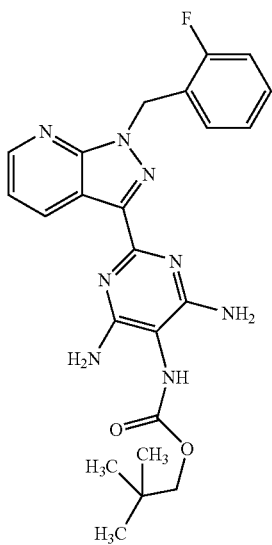

Prepared in analogy to Example 2 with 100 mg (0.29 mmol) of 2-[1-(2-fluorobenzyl)-1H-pyrazolo[3,4-b]pyridin-3-yl]-4,5,6-pyrimidinetriamine trihydrochloride from Example 8A, 5 ml of pyridine and 43 mg (0.29 mmol) of neopentyl chlorocarbonate.

Yield: 54 mg (41% of theory)

LC/MS (Method 1): $R_t$=3.10 min

MS (EI): m/z=465 (M+H)$^+$ $^1$H-NMR (400 MHz, DMSO-d$_6$): δ=0.95 (br. s, 9H), 3.74 (s, 2H), 5.79 (s, 2H), 6.10 (br. s, 4H), 7.08–7.17 (m, 2H), 7.22 (t, 1H), 7.29–7.39 (m, 2H), 8.00 (br. s, 1H), 8.60 (dd, 1H), 9.06 (dd, 1H).

Example 5

Methyl 4,6-diamino-2-[1-(2-fluorobenzyl)-1H-pyrazolo[3,4-b]pyridin-3-yl]-5-pyrimidinylcarbamate

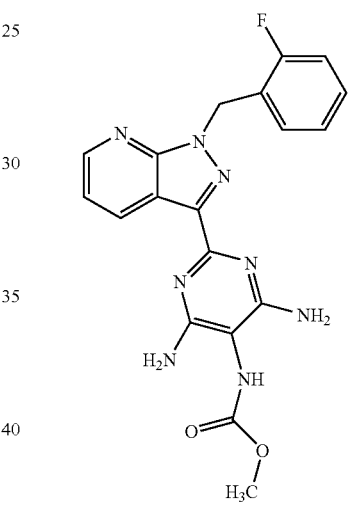

30.5 g (87.0 mmol) of 2-[1-(2-fluorobenzyl)-1H-pyrazolo[3,4-b]pyridin-3-yl]-4,5,6-pyrimidinetriamine trihydrochloride from Example 8A are dissolved in 30 ml of pyridine. The resulting solution is cooled to 0° C. 8.22 g (87.0 mmol) of methyl chloroformate are added, and the mixture is stirred at 0° C. for a further 2 hours. It is subsequently allowed to warm to room temperature and is stirred for a further 12 hours. After concentration in vacuo, the residue is washed with water and dried. Further purification is effected by stirring in 300 ml of boiling diethyl ether. The precipitated product is filtered off with suction and dried in vacuo.

Yield: 32.6 g (92% of theory)

LC/MS (Method 1): $R_t$=2.61 min

MS (EI): m/z=409 (M+H)$^+$ $^1$H-NMR (400 MHz, DMSO-d$_6$): δ=3.61 (s, 3H), 5.80 (s, 2H), 6.19 (br. s, 4H), 7.08–7.16 (m, 2H), 7.22 (t, 1H), 7.28–7.39 (m, 2H), 7.99 (br. s, 1H), 8.60 (dd, 1H), 9.05 (dd, 1H).

Example 6

Ethyl 4,6-diamino-2-[1-(2-fluorobenzyl)-1H-pyrazolo[3,4-b]pyridin-3-yl]-5-pyrimidinyl(methyl)carbamate

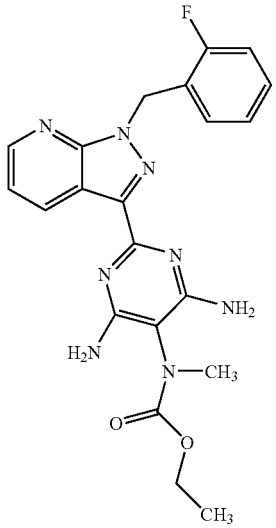

54 mg (0.13 mmol) of ethyl 4,6-diamino-2-[1-(2-fluorobenzyl)-1H-pyrazolo[3,4-b]pyridin-3-yl]-5-pyrimidinylcarbamate from Example 2 are added to 5 ml of DMF, the mixture is cooled to 0° C., and 7.67 mg (0.19 mmol) of sodium hydride are added. Then 18.14 mg (0.13 mmol) of iodomethane are added dropwise, and the mixture is stirred for one hour. The mixture is mixed with water and extracted with dichloromethane. The combined organic phases are dried over magnesium sulphate and concentrated in a rotary evaporator. The residue is purified first by column chromatography (mobile phase: dichloromethane/methanol=10:1) and then by preparative RP-HPLC.

Yield: 32 mg (58% of theory)
LC/MS (Method 2): $R_t$=2.91 min
MS (EI): m/z=437 (M+H)$^+$
$^1$H-NMR (200 MHz, DMSO-d$_6$): δ=1.08 (t, 3H), 2.99 (s, 3H), 2.93–4.11 (m, 2H), 5.79 (s, 2H), 6.35 (br. s, 4H), 7.06–7.14 (m, 2H), 7.16–7.28 (m, 1H), 7.28–7.32 (m, 2H), 8.59 (dd, 1H), 9.06 (dd, 1H).

Example 7

Isopropyl 4,6-diamino-2-[1-(2-fluorobenzyl)-1H-pyrazolo[3,4-b]pyridin-3-yl]-5-pyrimidinyl(methyl)carbamate

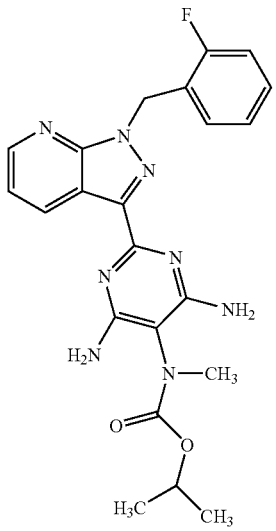

Prepared in analogy to Example 6 with 75 mg (0.17 mmol) of isopropyl-4,6-diamino-2-[1-(2-fluorobenzyl)-1H-pyrazolo[3,4-b]pyridin-3-yl]-5-pyrimidinylcarbamate from Example 3, 10.31 mg (0.26 mmol) of sodium hydride and 24.4 mg (0.17 mmol) of iodomethane. The residue is purified by preparative RP-HPLC.

Yield: 32 mg (41% of theory)
LC/MS (Method 1): $R_t$=2.97 min
MS (EI): m/z=451 (M+H)$^+$
$^1$H-NMR (300 MHz, DMSO-d$_6$): δ=1.09 (d, 6H), 2.98 (s, 3H), 4.80 (quin., 1H), 5.79 (s, 2H), 6.31 (br. s, 4H), 7.05–7.16 (m, 2H), 7.22 (t, 1H), 7.28–7.40 (m, 2H), 8.59 (dd, 1H), 9.07 (dd, 1H).

Example 8

Methyl 4,6-diamino-2-[1-(2-fluorobenzyl)-1H-pyrazolo[3,4-b]pyridin-3-yl]-5-pyrimidinyl(methyl)carbamate

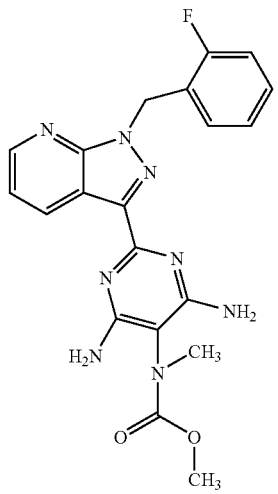

Prepared in analogy to Example 6 with 310 mg (0.76 mmol) of methyl-4,6-diamino-2-[1-(2-fluorobenzyl)-1H-pyrazolo[3,4-b]pyridin-3-yl]-5-pyrimidinylcarbamate from Example 5, 27.32 mg (1.14 mmol) of sodium hydride and 215.5 mg (1.52 mmol) of iodomethane. The mixture is worked up by adding water and 2 molar potassium hydroxide solution and extracting with dichloromethane. The combined organic phases are dried with magnesium sulphate and concentrated in a rotary evaporator. The residue is purified by preparative RP-HPLC.

Yield: 93 mg (29% of theory)
Larger amounts of the compound of Example 8 can be prepared by the following synthetic method:

20.0 g (49.0 mmol) of methyl 4,6-diamino-2-[1-(2-fluorobenzyl)-1H-pyrazolo[3,4-b]pyridin-3-yl]-5-pyrimidinylcarbamate from Example 5 are dissolved in 257 ml of tetrahydrofuran and cooled to 0° C. 53.9 ml (49.0 mmol of a 1M solution in tetrahydrofuran) of lithium bis(trimethylsilyl)amide are added dropwise over the course of 15 minutes. After stirring at 0° C. for 20 min, 6.95 g (53.9 mmol) of iodomethane are added. After one hour, the mixture is allowed to warm to room temperature, and the reaction is stopped by adding saturated aqueous ammonium chloride solution. The phases are separated. The aqueous phase is extracted several times with ethyl acetate and dichloromethane. The combined organic phases are concentrated in vacuo. The residue obtained in this way is suspended in a mixture of dichloromethane and tetrahydrofuran (1:1). The insoluble crystals are filtered off with suction and taken up in methanol. The mixture is refluxed for one hour. After cooling, the precipitate which has separated out is filtered off. The red solid obtained in this way is suspended in 100 ml of a mixture of dioxane and dichloromethane (1:1) and, while boiling, 20 ml of methanol are added until a clear solution forms. Activated carbon is added, and the mixture is boiled briefly and filtered hot through kieselguhr. The solution obtained in this way is evaporated to dryness. The suspension after taking up in methanol is stirred at room temperature for one hour. The white crystals are filtered off with suction.

Yield: 14.9 g (72% of theory)

LC/MS (Method 3): $R_t$=1.85 min

MS (EI): m/z=423 (M+H)$^+$ $^1$H-NMR (200 MHz, DMSO-d$_6$): δ=3.01 (s, 3H), 3.57 (s, 3H), 5.92 (s, 2H), 7.05.7.17 (m, 2H), 7.18–7.46 (m, 3H), 7.47–7.61 (m, 2H), 7.59–7.97 (m, 2H), 8.71–8.81 (m, 1H), 8.97 (dd, 1H).

Example 9

Isopropyl 4,6-diamino-2-[1-(2-fluorobenzyl)-1H-pyrazolo[3,4-b]pyridin-3-yl]-5-pyrimidinyl(ethyl) carbamate

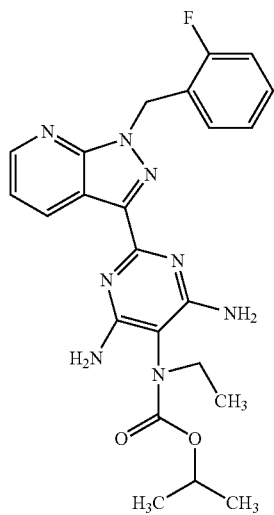

Prepared in analogy to Example 6 with 60 mg (0.14 mmol) of isopropyl 4,6-diamino-2-[1-(2-fluorobenzyl)-1H-pyrazolo[3,4-b]pyridin-3-yl]-5-pyrimidinylcarbamate from Example 3, 4.95 mg (0.21 mmol) of sodium hydride and 21.4 mg (0.17 mmol) of iodoethane. To complete the reaction, the same amount of sodium hydride and iodoethane are added once again. The residue is purified by preparative RP-HPLC.

Yield: 43 mg (67% of theory)

LC/MS (Method 1): $R_t$=2.97 min

MS (EI): m/z=465 (M+H)$^+$ $^1$H-NMR (200 MHz, DMSO-d$_6$): δ=0.96–1.06 (m, 3H), 1.09 (d, 6H), 2.79–2.93 (m 2H), 4.82 (quin., 1H), 5.80 (s, 2H), 6.25 (br. s, 4H), 7.01–7.14 (m, 2H), 7.15–7.50 (m, 3H), 8.60 (dd, 1H) 9.09 (dd, 1H).

The invention claimed is:

1. A compound of the formula (I)

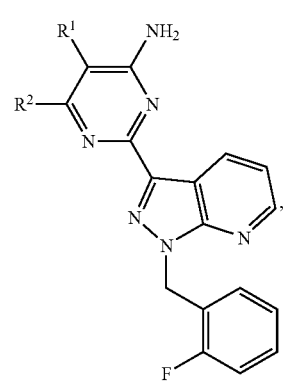

in which $R^1$ is —NR$^3$C(=O)OR$^4$, $R^2$ is hydrogen or NH$_2$, $R^3$ is hydrogen or (C$_1$–C$_4$)-alkyl, $R^4$ is (C$_1$–C$_6$)-alkyl, or a salt or hydrate thereof.

2. The compound of claim 1, in which $R^1$ is —NR$^3$C(=O)OR$^4$, $R^2$ is hydrogen or NH$_2$, $R^3$ is (C$_1$–C$_4$)-alkyl, $R^4$ is (C$_1$–C$_4$)-alkyl, or a salt or hydrate thereof.

3. The compound of claim 1, in which $R^1$ is —NR$^3$C(=O)OR$^4$, $R^2$ is NH$_2$, $R^3$ is methyl or ethyl, $R^4$ is methyl, ethyl or isopropyl, or a salt or hydrate thereof.

4. The compound of claim 1 having the following structure:

methyl 4,6-diamino-2-[1-(2-fluorobenzyl)-1H-pyrazolo[3,4-b]pyridin-3-yl]-5-pyrimidinyl(methyl)carbamate

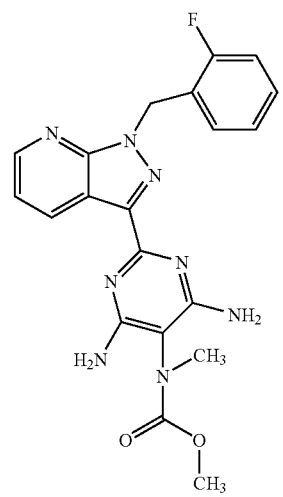

or a salt or hydrate thereof.

5. The compound of claim 1, wherein said compound is methyl 4,6-diamino-2-[1-(2-fluorobenzyl)-1H-pyrazolo[3,4-b]pyridin-3-yl]-5-pyrimidinylcarbamate:

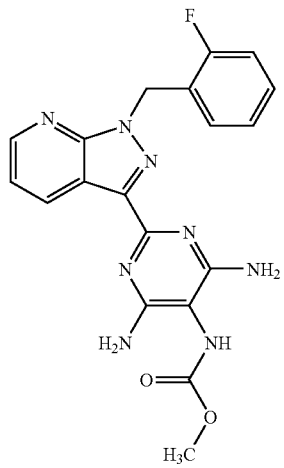

or a salt or hydrate thereof.

6. A process for the preparation of compounds of the formula (I) as defined in claim 1, characterized in that either

[A] a compound of the formula (Ia)

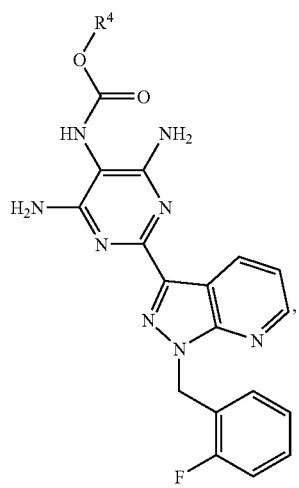

(Ia)

in which
$R^4$ is as defined in claim 1,
is reacted with a compound of the formula (II)

$R^3$—$X^1$     (II), in which
$R^3$ is as defined in claim 1, and
$X^1$ is a leaving group,
or

[B] the compound of the formula (III)

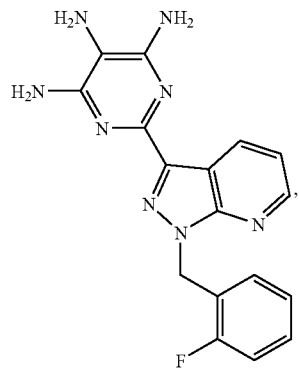

(III)

is reacted with a compound of the formula (IV)

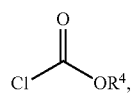

(IV)

in which
$R^4$ is as defined in claim 1,
or

[C] the compound of the formula (V)

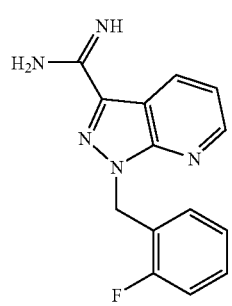

(V)

is reacted with a compound of the formula (VI)

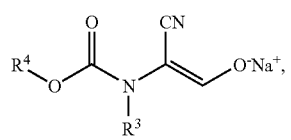

(VI)

in which
R³ and R⁴ are as defined in claim 1,
to give a compound of the formula (Ib)

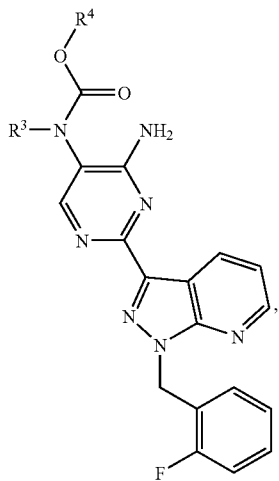

in which
R³ and R⁴ are as defined in claim 1.

7. A pharmaceutical composition comprising at least one compound of the formula (I) as defined in claim 1, and at least one further excipient.

8. A pharmaceutical composition comprising at least one compound of the formula (I) as defined in claim 1 in combination with at least one organic nitrate or NO donor.

9. A pharmaceutical composition comprising at least one compound of the formula (I) as defined in claim 1 in combination with at least one compound which inhibits the breakdown of cyclic guanosine monophosphate (cGMP).

10. A method for the treatment of hypertension, comprising administering to a patient in need thereof a therapeutically effective amount of a compound of claim 1.

11. A method for the treatment of sexual dysfunction, comprising administering to a patient in need thereof a therapeutically effective amount of a compound of claim 1.

12. The method of claim 10 or 11, where compounds of the formula (I) as defined in claim 1 are employed in combination with at least one organic nitrate or NO donor or in combination with at least one compound which inhibits the breakdown of cyclic guanosine monophosphate (cGMP).

13. The method of claim 11, wherein the sexual dysfunction is erectile dysfunction or female sexual dysfunction.

* * * * *